US007951982B2

(12) United States Patent
Mukhopadhyay et al.

(10) Patent No.: US 7,951,982 B2
(45) Date of Patent: *May 31, 2011

(54) METHOD FOR PRODUCING FLUORINATED ORGANIC COMPOUNDS

(75) Inventors: Sudip Mukhopadhyay, Williamsville, NY (US); Haridasan K. Nair, Williamsville, NY (US); Hsueh S. Tung, Getzville, NY (US); Michael Van Der Puy, Amherst, NY (US); Robert C. Johnson, Lancaster, NY (US); Daniel C. Merkel, West Seneca, NY (US)

(73) Assignee: Honeywell International Inc., Morristown, NJ (US)

( * ) Notice: Subject to any disclaimer, the term of this patent is extended or adjusted under 35 U.S.C. 154(b) by 369 days.

This patent is subject to a terminal disclaimer.

(21) Appl. No.: 11/592,842

(22) Filed: Nov. 3, 2006

(65) Prior Publication Data

US 2007/0112227 A1   May 17, 2007

Related U.S. Application Data

(63) Continuation-in-part of application No. 11/118,504, filed on Apr. 29, 2005, now Pat. No. 7,371,904, and a continuation-in-part of application No. 11/118,503, filed on Apr. 29, 2005, now Pat. No. 7,345,209, and a continuation-in-part of application No. 11/118,530, filed on Apr. 29, 2005, now Pat. No. 7,189,884.

(60) Provisional application No. 60/567,426, filed on Apr. 29, 2004, provisional application No. 60/567,429, filed on Apr. 29, 2004, provisional application No. 60/567,427, filed on Apr. 29, 2004, provisional application No. 60/567,425, filed on Apr. 29, 2004, provisional application No. 60/567,428, filed on Apr. 9, 2004, provisional application No. 60/733,379, filed on Nov. 3, 2005.

(51) Int. Cl.
C07C 21/18 (2006.01)

(52) U.S. Cl. .................. 570/171; 570/136; 570/159

(58) Field of Classification Search .................. None
See application file for complete search history.

(56) References Cited

U.S. PATENT DOCUMENTS

| | | | |
|---|---|---|---|
| 2,931,840 A | 4/1960 | Marquis | |
| 2,996,555 A | 8/1961 | Rausch et al. | |
| 3,472,826 A | 10/1969 | Potts et al. | |
| 3,659,023 A | 4/1972 | Regan | |
| 4,086,407 A | 4/1978 | Fozzard | |
| 4,650,914 A | 3/1987 | Woodard | |
| 4,798,818 A | 1/1989 | Baizer et al. | |
| 4,900,874 A | 2/1990 | Ihara et al. | |
| 5,162,594 A | 11/1992 | Krespan | |
| 5,532,419 A | 7/1996 | Van Der Puy et al. | |
| 5,545,777 A | 8/1996 | Morikawa et al. | |
| 5,574,192 A | 11/1996 | Van Der Puy et al. | |
| 5,608,126 A | 3/1997 | Morikawa et al. | |
| 5,679,875 A | 10/1997 | Aoyama et al. | |
| 5,710,382 A | 1/1998 | Dunmead et al. | |
| 5,969,198 A | 10/1999 | Thenappan et al. | |
| 5,986,151 A | 11/1999 | Van Der Puy | |
| 6,023,004 A | 2/2000 | Thenappan et al. | |
| 6,031,141 A | 2/2000 | Malikarjuna et al. | |
| 6,066,769 A | 5/2000 | Nappa et al. | |
| 6,111,150 A | 8/2000 | Sakyu et al. | |
| 6,124,510 A | 9/2000 | Elsheikh et al. | |
| 6,369,284 B1 | 4/2002 | Nappa et al. | |
| 6,521,802 B1 * | 2/2003 | Takubo et al. | ................ 570/167 |
| 6,548,719 B1 | 4/2003 | Nair et al. | |
| 6,809,226 B1 | 10/2004 | Pennetreau et al. | |
| 6,958,424 B1 | 10/2005 | Nair et al. | |
| 6,977,316 B1 | 12/2005 | Mukhopadhyay et al. | |
| 7,026,520 B1 | 4/2006 | Mukhopadhyay et al. | |
| 7,026,521 B1 | 4/2006 | Mukhopadhyay et al. | |
| 7,071,367 B1 | 7/2006 | Mukhopadhyay et al. | |
| 7,132,578 B1 | 11/2006 | Mukhopadhyay et al. | |
| 7,135,601 B2 | 11/2006 | Mukhopadhyay et al. | |
| 7,189,884 B2 | 3/2007 | Mukhopadhyay et al. | |
| 7,196,236 B2 | 3/2007 | Mukhopadhyay et al. | |
| 7,345,209 B2 * | 3/2008 | Mukhopadhyay et al. | ... 570/157 |
| 7,371,904 B2 * | 5/2008 | Ma et al. | ....................... 570/136 |
| 2003/0060670 A1 | 3/2003 | Nair et al. | |
| 2004/0119047 A1 | 6/2004 | Singh et al. | |
| 2005/0020862 A1 | 1/2005 | Tung et al. | |

(Continued)

FOREIGN PATENT DOCUMENTS

EP          0522639          1/1993

(Continued)

OTHER PUBLICATIONS

Banks, et al., Journal of Fluorine Chemistry, vol. 82, Issue 2, pp. 171-174 (1997).

(Continued)

Primary Examiner — Daniel M Sullivan
Assistant Examiner — Yevegeny Valenrod
(74) Attorney, Agent, or Firm — Bruce Bradford

(57) ABSTRACT

Disclosed is a process for the preparation of fluorinated olefins. In preferred embodiments C3 olefins are produced by methods comprising contacting a compound of the Formula (I)

$$C(R^1_aR^2_bR^3_c) \qquad (I)$$

with a compound of Formula (II)

$$C(R^1_aR^2_bR^3_c)C_n(R^1_aR^2_bR^3_c) \qquad II$$

wherein $R^1_a$, $R^2_b$, and $R^3_c$ are independently a hydrogen atom or a halogen selected from the group consisting of fluorine; chlorine, bromine and iodine, provided that the compound of formula I has at least three halogen substituents and that said at three halogen substituents comprise at least one fluorine; a, b and c are independently=0, 1, 2 or 3 and (a+b+c)=2 or 3; and n is 0 or 1, under conditions effective to produce at least one C3 fluoroolefin.

25 Claims, No Drawings

U.S. PATENT DOCUMENTS

| | | |
|---|---|---|
| 2005/0080302 A1 | 4/2005 | Baker et al. |
| 2005/0090698 A1 | 4/2005 | Merkel et al. |
| 2005/0171391 A1 | 8/2005 | Janssens et al. |
| 2007/0112228 A1 | 5/2007 | Mukhopadhyay et al. |
| 2007/0112229 A1 | 5/2007 | Mukhopadhyay et al. |
| 2007/0112230 A1 | 5/2007 | Mukhopadhyay et al. |
| 2007/0129580 A1 | 6/2007 | Mukhopadhyay et al. |

FOREIGN PATENT DOCUMENTS

| | | |
|---|---|---|
| EP | 0644173 | 3/1995 |
| EP | 0729932 A1 | 9/1996 |
| EP | 974571 A2 | 1/2000 |
| GB | 844597 | 8/1960 |
| JP | 11140002 | 5/1999 |
| JP | 2000169404 | 6/2000 |
| JP | 2000178543 | 6/2000 |
| WO | 9008752 | 8/1990 |
| WO | 9504021 | 2/1995 |
| WO | 96/01797 A | 1/1996 |
| WO | 98/42645 | 3/1998 |
| WO | 98/21171 | 5/1998 |
| WO | 99/48993 | 9/1999 |
| WO | 00/39242 | 7/2000 |
| WO | 01/07384 | 2/2001 |
| WO | 03027051 | 4/2003 |
| WO | 2005/012212 | 2/2005 |
| WO | 2005/042451 A | 5/2005 |
| WO | 2005108332 | 11/2005 |
| WO | 2005108334 | 11/2005 |
| WO | 2007019355 A | 2/2007 |

OTHER PUBLICATIONS

Database Beilstein, Beilstein Institute for Organic Chemistry, M. Van Der Puy: J. Fluorine Chemistry, vol. 81, No. 2, 1997, pp. 187-192 XP002424669.

Database Beilstein, Beilstein Institute for Organic Chemistry, Haszeldine, Steele: J. Chem. Soc. 1953, p. 1592, 1597, XP0022424670.

Database WPI Week 199812, AN 1998-126110, XP002427152, Derwent Publications Ltd., London, GB & JP 10 007605A (Central Glass Co Ltd) Jan. 13, 1998 abstract.

Dickson, R.S., Fluorcarbon-Aluminium Compounds, Aust. J. Chem., 1972, 25, 761-8.

Gambareto et al., "The Reaction of chlorine monofloride with unsaturated compounds", 1976, XP00246119.

Henne, Albert L., et al., Chlorinated Derivatives of 2-Floropropane[1] J. American Chemical Society, Jul. 11, 1941: pp. 2692-2694, vol. 63.

Knunyants, I. L. et al. Reaction of Fluoro Olefins, Institute of Heteroorganic Compounds, Bulletin of the Academy of Sciences of USSR, Division of Chemical Sciences -ISSN 0568-5230, p. 1312-1317.

March, J. Advanced Organic Chemistry, 1997, pp. 631-636, McGraw-Hill International Book Company, XP002427150.

Vittorio Minanari, A Novel Systensis of Perhalogenated Alkenes, J. Org. Chem. 1992, 57, 5018-5019.

B.V. Kunshenko, et al., "Reaction of Organic Compounds With SF4-HF-Halogenating System," Journal of Organic Chemistry of the USSR, vol. 28, No. 4 pp. 672-680, Apr. 1992. RU.

Robert P. Salmon et al., "Experimental Flow Tube Study on Pyrolysis of 2-Chloro-1,1,1-Trifluoroethane," Article, Department of Chemical Engineering, Villanova University, XP-001120412, pp. 507-510 (1996). US.

Database Belstein XP-002426121 (1951, 1952, 1998).

R.N. Haszeldine et al., "Free-radical Additions to Unsaturated Systems. Part XVII. Reaction of Trifluoroiodomethane with Mixtures of Ethylene and Vinyl Fluoride and of Ethylene and Propene," J. Chem. Soc. (C), pp. 414-421 (1970).

J. Burdon et al., J. Fluorine Chemistry; EN; 40; pp. 283-318; XP-002424668. (1988).

M.P. Knunyants et al., "Reactions of Fluoro Olefins; Communication 13. Catalytic Hydrogenation of Periluoro Olefins," Institute of Heteroorganic Compounds, Bulletin of the Academy of Sciences of the USSR, Division of Chemical Sciences, pp. 1312-1317; XP-000578879 (original article Mar. 3, 1959).

* cited by examiner

METHOD FOR PRODUCING FLUORINATED ORGANIC COMPOUNDS

CROSS-REFERENCES TO RELATED APPLICATIONS

This application claims the priority benefit of U.S. Provisional Application No. 60/733,379, filed Nov. 3, 2005 and is a Continuation-in-Part of U.S. patent application Ser. No. 11/118,503, (now U.S. Pat. No. 7,345,209) filed on Apr. 29, 2005, which in turn claims the priority benefit of U.S. Provisional Patent Application Nos. 60/567,427 and 60/567,425 filed Apr. 29, 2004.

U.S. Provisional Patent Application Nos. 60/567,427 and 60/567,425 filed Apr. 16, 2004. This application is also a Continuation-in-Part of U.S. patent application No. 11/118,504, (now U.S. Pat. No. 7,371,904) filed on Apr. 29, 2005, which in turn claims the priority benefit of U.S. Provisional Patent Application Nos. 60/567,426 and 60/567,429 filed Apr. 29, 2004.

This application is also a Continuation-in-Part of U.S. patent application Ser. No. 11/118,504, (now U.S. Pat. No. 7,189,884) filed on Apr. 29, 2005, which in turn claims the priority benefit of U.S. Provisional Patent Application No. 60/567,428 filed on Apr. 29, 2004.

The disclosures of each of the above-mentioned applications are incorporated herein by reference. Also incorporated herein by reference are U.S. Provisional Patent Application Nos. 60/733,444; 60/733,383; 60/733,355; 60/733,372 and 60/733,378, each of which was filed on Nov. 3, 2005.

BACKGROUND OF INVENTION

1. Field of Invention

This invention relates to novel methods for preparing fluorinated organic compounds, and more particularly to methods of producing fluorinated olefins.

2. Description of Related Art

Hydrofluorocarbons (HFC's), in particular hydrofluoroalkenes such tetrafluoropropenes (including 2,3,3,3-tetrafluoro-1-propene (HFO-1234yf) and 1,3,3,3-tetrafluoro-1-propene (HFO-1234ze)) have been disclosed to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFCs do not contain chlorine and thus pose no threat to the ozone layer.

Several methods of preparing hydrofluoroalkanes are known. For example, U.S. Pat. No. 4,900,874 (Ihara et al) describes a method of making fluorine containing olefins by contacting hydrogen gas with fluorinated alcohols. Although this appears to be a relatively high-yield process, for commercial scale production the handling of hydrogen gas at high temperature raises difficult safety related questions. Also, the cost of producing hydrogen gas, such as building an on-site hydrogen plant, can be prohibitive in many situations.

U.S. Pat. No. 2,931,840 (Marquis) describes a method for making fluorine containing olefins by pyrolysis of methyl chloride and tetrafluoroethylene or chlorodifluoromethane. This process is a relatively low yield process and a relatively large percentage of the organic starting material is converted in this process to unwanted and/or relatively unimportant byproducts, including a sizeable amount of carbon black. The carbon black is not only unwanted, it tends to deactivate the catalyst used in the process.

The preparation of HFO-1234yf from trifluoroacetylacetone and sulfur tetrafluoride has been described. See Banks, et al., *Journal of Fluorine Chemistry*, Vol. 82, Iss. 2, p. 171-174 (1997). Also, U.S. Pat. No. 5,162,594 (Krespan) discloses a process wherein tetrafluoroethylene is reacted with another fluorinated ethylene in the liquid phase to produce a polyfluoroolefin product.

Catalyzed hydrogen reduction reactions have been disclosed for the preparation of fluorinated C3 hydrocarbons in U.S. Pat. No. 5,545,777. The patent describes the reaction as being one in which a compound of formula (1)

$$C3H_aCl_bF_c \qquad (1)$$

is converted by catalyzed hydrogen reduction to a compound of formula (2)

$$C_3H_{a+x}Cl_{b-y}F_{c-z} \qquad (2)$$

where a, b, c, x, y and z are integers satisfying the following conditions:
$a \geq 0$, $b \geq 1$, $c \geq 2$, $x \geq 1$, $y \geq 1$, $z \geq 0$, $a+b+c=8$, $x=y+z$, $b-y \geq 0$, and $c-z \geq 2$. Since the reactions disclosed in this patent require a reaction product in which $a+b+c=8$ and that $x=y+z$, the disclosed reaction product does not include C3 olefins, which as mentioned above have been found to be desirable for use in many important applications.

Notwithstanding prior teachings, applicants have come to appreciate a continuing need for methods for efficiently preparing certain hydrofluorocarbons, particularly halogenated olefins such as the fluorinated propenes, including HFO-1234yf.

SUMMARY OF THE INVENTION

Applicants have developed methods for producing fluorinated organic compounds, including hydrofluoropropenes, which preferably comprise contacting a compound of the Formula (I)

$$C(R^1_aR^2_bR^3_c) \qquad (I)$$

with a compound of Formula (II)

$$C(R^1_aR^2_bR^3_c)C_n(R^1_aR^2_bR^3_c) \qquad (II)$$

wherein $R^1_a$, $R^2_b$, and $R^3_c$ are each independently H or a halogen selected from the group consisting of fluorine; chlorine, bromine and iodine, provided that the compound of Formula I has at least three halogen substituents and that said at least three halogen substituents comprise at least one fluorine; a, b and c are each independently=0, 1, 2 or 3 and (a+b+c)=2 or 3; and n is 0 or 1.

In preferred embodiments, the methods of the present invention carry out such a contacting step under conditions effective to produce at least one polyfluorinated C2-C6 olefin, more preferably a polyfluorinated propene, and even more preferably at least one tetrafluoropropene.

The preferred contacting step of the present invention comprises a catalytic reaction which, in preferred embodiments, comprises introducing at least one compound of Formula (I) and at least one compound of Formula (II) to a reaction system under conditions effective to convert, and preferably convert at least about 50%, more preferably at least about 70%, and even more preferably at least about 90%, of said compound of Formula (II). It is also generally preferred that said converting step produces a reaction product having at least about 20% selectivity, more preferably at least about 40% selectivity and even more preferably at least about 70% selectivity to polyfluorinated C2-C6 olefins, more preferably polyfluorinated propenes, and even more preferably tetrafluoropropenes. In highly preferred embodiments said converting step produces a reaction product having at least about 20% selectivity, more preferably at least about 40% selectivity and even more preferably at least about 70% selectivity HFO-1234yf.

In certain preferred embodiments, the converting step comprises reacting a compounds of Formula (I) and Formula (II) in the gas phase, in the liquid phase, or a combination of these, with gas phase reactions preferably occurring in the presence of catalyst.

DETAILED DESCRIPTION OF PREFERRED EMBODIMENTS

One beneficial aspect of the preferred form of the present invention is that it enables the production of desirable fluoroolefins, preferably C3 fluoroolefins, using relatively high conversion and high selectivity reactions. In addition, the preferred embodiments of the present methods provide reactions with relatively high yield and which are capable of obtaining relatively long catalyst life.

Furthermore, the present methods in certain preferred embodiments permit the products of the desirable fluoroolefins from relatively attractive starting materials. Methane and its derivatives, ethane and its derivates, and CFCs may in certain embodiments be an advantageous starting materials because many of such products are relatively easy to handle, and/or are generally readily available in commercial quantities, and/or can be easily produced from other readily available materials.

In certain preferred embodiments, the contacting step comprises contacting, (preferably by introducing into a reactor) one or more compounds of Formula (I) and one or more compounds of Formula (II) in a Formula (II):Formula (I) mole ratio of from about 0.5:1 to about 10:1, and even more preferably of from about 1:1 to about 3:1. In preferred embodiments in which the Formula (I) compound comprises $CF_3Cl$ and the Formula (II) compound comprises $CH_3CF_2Cl$, the $CH_3CF_2Cl:CF_3Cl$ mole ratio of the feed(s) to the reactor are from about 1:1 to about 4:1 and even more preferably from about 1.5:1 to about 2.5:1. In many preferred embodiments the contacting step takes place in a single vessel and is considered to be a one-step reaction. We have surprisingly discovered that in many embodiments the presence of air, or other oxygen-containing material, in the feed to the reactor is highly preferred. Without necessarily being bound by to any particular theory of operation, it is believed that advantage is achieved in such embodiments because carbon is detrimentally deposited on the catalyst surface in the absence of air or its principal components. Without intending to be bound by or limited to any particular theory of operation, it is believed that in certain embodiments the reaction proceeds via the formation of $CF_3CF_2CH_3$ (HFC-245cb), which is quickly or substantially instantaneously dehydrofluorinated to HFO-1234yf under the preferred reaction conditions of the present invention. Another aspect of this not limiting theory is that the mechanism of this embodiment of the present invention is understood and believed to be that the reaction is initiated by the heterolytic clevage of the C—Cl bonds in chlorodifluoroethane (HCFC-142b) and similar compounds, such as chlortrifluoromethane (CFC-13).

In other embodiments, it is preferred that the contacting step comprises oxidative coupling of compound(s) of Formula (I) and Formula (II), particularly in embodiments in which the compound of Formula (I) is methane or one of its halogenated derivatives (such as methyl chloride) and the compound of Formula (II) is a chlorofluorohydrocarbon (HCFC) or chlorofluorocarbon (CFC), and preferably C1 and C2 HCFCs and/or CFC. Preferably the reaction product includes, in high yield and high selectivity, tetrafluoropropene(s), and even more preferably HFO-1234yf. As with the particular embodiments mentioned above, it is desirable and highly preferred in certain situations to include air or its principal components in the feed stream to the reactor in order to enhance catalyst life and effectiveness.

It is generally preferred that this reaction step be carried out in the gas phase, or in some embodiments possibly a combination of liquid/gas phases, and it is further contemplated that the reaction can be carried out batch wise, continuous, or a combination of these.

Thus, it is contemplated that the preferred contacting steps may be preformed using a wide variety of process parameters and process conditions in view of the overall teachings contained herein. However, it is preferred in certain embodiments that the contacting step includes a reaction step comprising a gas phase reaction, preferably in the presence of catalyst, supported on carbon or unsupported, preferably a metal-based catalyst, and even more preferably a nickel based catalyst (such as nickel mesh) and/or palladium-based catalyst, including palladium on carbon catalysts. It is contemplated, although not necessarily preferred at the present time, that other catalysts, such as antimony-based catalysts (including $SbF_3$, $SbF_5$, and partially flourinated $SbCl_3$ or $SbCl_5$), aluminum-based catalyst (such as $AlCl_3$), iron-based catalyst (such FeCl3), including such catalysts on a carbon or other appropriate support, may be used in accordance with the present invention. It is expected that many other catalysts may be used depending on the requirements of particular embodiments, and of course, two or more of any of these catalysts, or other catalysts not named here, may be used in combination.

The gas phase addition reaction may be conducted, for example, by introducing a gaseous form of a compound of Formula (I) and Formula (II) into a suitable reaction vessel or reactor. Preferably the vessel is comprised of materials which are resistant to corrosion, such as Hastelloy, Inconel, Monel and/or fluoropolymers linings. Preferably the vessel contains catalyst, for example a fixed or fluid catalyst bed, packed with a suitable addition catalyst, with suitable means to heat and/or cool the reaction mixture to the desired reaction temperature.

While it is contemplated that a wide variety of reaction temperatures and pressures may be used, depending on relevant factors such as the catalyst being used and the most desired reaction product, it is generally preferred that at least a portion of the reaction step is carried out at a reaction temperature of from about 5° C. to about 1000° C., and even more preferably from about 400° C. to about 800° C., and even more preferably from about 450° C. to about 700° C. for reactors which are preferably maintained at a pressure of from about 1 to about 1500 psig, more preferably from about 1 psig to about 50 psig, and even more preferably from about 1 to about 10 psig.

In preferred embodiments the conversion of the Formula (II) compound is preferably at least about 15%, more preferably at least about 40%, and selectivity to tetrafluoropropene compounds is preferably at least about 1%, more preferably at least about 5%, and even more preferably at least about 20%.

A. Contacting Step—Formula (II) Comprises $CH_3CF_2Cl$

Applicants have discovered that Formula (II) compounds, such as the preferred $CH_3CF_2Cl$, can be reacted with compounds of Formula (I), such as the preferred $CF_3Cl$, to synthesize tetrafluorinated compounds such as the preferred $CF_3CF=CH_2$ (HFO-1234yf). In certain preferred embodiments, the contacting step includes a reaction of the type in which a certain flow of the compound of Formula (II), such as about 50 sccm of $CH_3CF_2Cl$, together with a flow of the compound of Formula (I), such as about 20 sccm of CF3Cl, is introduced together with a flow of air (e.g., about 20 sccm) into a reaction vessel, which may include a pre-heater operating at a relatively elevated temperature, for example, from about 400° C. to about 800° C. (preferably in certain embodiments at about 450° C.) containing the appropriate amount and type of catalyst in accordance with the present invention (for gas flows of the quantity mentioned in this paragraph, a bed of about 50 cc of catalyst in a 1-inch Monel reactor at about 675° C.). In certain embodiments, the effluent gas mixtures from the reactor may be passed through a 20% aqueous KOH solution to neutralize any HF formed during the reaction to KF and $H_2O$.

Catalyst Preparation

Certain preferred methods for catalyst preparation are described below, and the catalysts prepared in accordance with this description were used in and are referred to in the experiments described in the examples which follow.

Catalyst A

About 50 cc Ni-mesh is charged in the reactor and then reduced with 20 sccm of $H_2$ at about 650° C. for about 6 hours. This pre-reduced catalyst is preferably used in certain embodiments of the reaction in accordance with the present invention.

Catalyst B

About 50 cc Ni-mesh was used as the catalyst without $H_2$ pre-treatment.

Catalyst C

From about 1.5 gm to about 2.0 gm of Ni (II) hexafluoroacetylacetonate hydrate was dissolved in about 200 cc of methanol at about 55° C. and then 50 cc of dried activated carbon (⅛-inch cylinders) was gradually mixed with the precursor solution. The methanol was evaporated slowly under vacuum at room temperature and then dried in an oven under vacuum at about 100° C. for 10 hours.

The dried mass was then charged into the 1-inch Monel reactor and then reduced with 20 sccm of H2 at 550° C. for 6 hours and then 2 hours at 650° C. The catalyst was finally then calcined under 20 sccm of $N_2$ at 700° C. for about ½ hour.

Catalyst D

About 5 gm of $La_2NiO_4$ was prepared using the citric acid complexing method. Stoichiometric amounts of nickel and lanthanum nitrates were dissolved in an aqueous solution. After a small excess of citric acid was added, the solution was evaporated by vigorously stirring at about 70° C. to generate viscous syrup. To this syrup was added about 50 ml of methanol and about 50 cc of dried activated carbon. The resultant material was then dried in an oven at about 180° C. for about 1 hour, followed by calcinations at 500° C. for 2 hours and then at about 900° C. for about 6 hours. The catalyst was finally reduced with about 25 sccm of $H_2$ at about 750° C. for 8 hours.

Catalyst E

Pd/C was prepared using 3 gm of Pd (II) acetylacetonate as the precursor, and then the procedure used to prepare catalyst C was used.

Catalyst F

Powdered BaO was obtained from Aldrich and used after drying at about 450° C. under about 20 sccm of $N_2$ for about 12 hours.

Catalyst G

Powder 50 cc BaO was dispersed in an anhydrous solvent and then added a colloidal solution of about 1.3 gm of Ni in methanol to the mixture. The solvent was evaporated slowly under vacuum at room temperature and then dried in an oven under vacuum at about 100° C. for 10 hours. The dried mass was then charged into a 1-inch Monel reactor and then dried at about 550° C. for 6 hour and then calcined under 20 sccm of $N_2$ at 700° C. for ½ hour.

Catalyst H

About 50 cc of powder CaO was dispersed in an anhydrous solvent, and then a colloidal solution of about 1.3 gm of Ni in methanol was added to the mixture. The solvent was evaporated slowly under vacuum at room temperature and then dried in an oven under vacuum at 100° C. for 10 hours. The dried mass was then charged into a 1-inch Monel reactor and then dried at 550° C. for 6 hours and then calcined under about 20 sccm of $N_2$ at 700° C. for about ½ hour.

Catalyst I

About 50 cc of powder MgO was dispersed in an anhydrous solvent and then a colloidal solution of about 1.3 gm of Ni in methanol was added to the mixture. The solvent was evaporated slowly under vacuum at about room temperature and then dried in an oven under vacuum at about 100° C. for about 10 hours. The dried mass was then charged into the 1-inch monel reactor and dried at 550° C. for 6 hours and then calcined under 20 sccm of $N_2$ at 700° C. for about ½ hour.

Examples

Section A

Table A1 below shows results from experiments using as a first combination of reactants $CH_3CF_2Cl$ and $C_2F_6$ and a second combination of reactants comprising $CH_3CF_2Cl$ and $CF_3Cl$ under substantially identical conditions. The reaction between $CF_3Cl$ and $CH_3CF_2Cl$ gave about 16 mol % $CF_3CF=CH_2$ (HFO-1234yf) at a $CH_3CF_2Cl$ conversion level of about 72%. For reactions in which $CF_3Cl$ was replaced by $C_2F_6$, only trace amount of HF)-1234yf were obtained. It was also learned that in the presence of air, $CO_2$ was one of the major byproducts, whereas carbon black was one of the main byproducts in the absence of air or its principal constituents.

TABLE A1

Effect of different starting materials on the R1234yf production rate[a]

| Reaction | T, ° C. | P, psig | Conv. mol % | R1234yf mol % | Byproducts mol % |
|---|---|---|---|---|---|
| $CH_3CF_2Cl$ + $CF_3Cl$ + Air | 675 | 2.6 | 72 | 16 | $CO_2$(20%); C (5%); R1132 (12%); R143a(8%); R1131(12%); R134a(3%); R133a(2%); R22 (1%); R1130 (4%); R40 (5%); R1243 (1%); Unknown (11%) |
| $CH_3CF_2Cl$ + $C_2F_6$ + Air | 675 | 2.8 | 57 | 1.5 | $CO_2$(42%); C(10%); R115a (15%); R114a(21%); R22 (2%); R1112a (1%); R113a(1%); R123a (2%), Unknown(4.5%) |

[a]Reaction conditions: $CH_3CF_2Cl$, 50 SCCM; $CF_3Cl$, 20 SCCM; Air, 15 SCCM; Catalyst, G; Amount of catalyst, 50 cc; Conversion is the ratio of moles of CFC converted and moles of CFC taken initially × 100; 1234yf% = Moles of CFC converted to 1234yf/total moles of CFC taken initially × 100

Table A2 shows the effect of process parameters such as reaction temperature, pressure, flow rates, and composition of catalysts on the reaction. The highest conversion to the product HFO-1234yf (that is, about 16%) was obtained using the conditions given in Table 2, Run 2 using Catalyst G.

TABLE A2

Reaction of $CH_3CF_2Cl$ and $CF_3Cl$ in the presence of Air and catalyst[a]

| Run | T, °C. | P, psig | $CH_3CF_2Cl$, SCCM | $CF_3Cl$, SCCM | Air, SCCM | Cat | Conv. of $CH_3CF_2Cl$, mol % | Conv. to 1234yf, mol % |
|---|---|---|---|---|---|---|---|---|
| 1 | 600 | 3 | 50 | 20 | 15 | G | 57 | 7 |
| 2 | 675 | 3 | 50 | 20 | 15 | G | 72 | 16 |
| 3 | 700 | 3 | 50 | 20 | 15 | G | 83 | 12 |
| 4 | 675 | 10 | 50 | 20 | 15 | G | 73 | 14 |
| 5 | 675 | 15 | 50 | 20 | 15 | G | 75 | 12 |
| 6 | 675 | 3 | 30 | 20 | 15 | G | 62 | 9 |
| 7 | 675 | 3 | 70 | 20 | 15 | G | 53 | 16 |
| 8 | 675 | 3 | 50 | 20 | 15 | G | 68 | 16 |
| 9 | 675 | 3 | 50 | 40 | 15 | G | 63 | 16 |
| 10 | 675 | 3 | 50 | 20 | 5 | G | 53 | 9 |
| 11 | 675 | 3 | 50 | 20 | 40 | A | 57 | 3 |
| 12 | 675 | 3 | 50 | 20 | 15 | B | 49 | 1 |
| 13 | 675 | 3 | 50 | 20 | 15 | C | 80 | 9 |
| 14 | 675 | 3 | 50 | 20 | 15 | D | 83 | 11 |
| 15 | 675 | 3 | 50 | 20 | 15 | E | 57 | 0 |
| 16 | 675 | 3 | 50 | 20 | 15 | F | 68 | 6 |
| 17 | 675 | 3 | 50 | 20 | 15 | H | 58 | 8 |
| 18 | 675 | 3 | 50 | 20 | 15 | I | 84 | 12 |

[a]Catalyst A is Ni-mesh reduced; B is Ni-mesh; C is Ni/C; D is $La_2NiO_4$; E is Pd/C; F is BaO; G is Ni/BaO; H is Ni/CaO; I is Ni/MgO Without intending to be bound by her to any particular theory, it is believed that the reaction mechanism is as follows:

$CH_3CF_2Cl \leftrightarrow CH_3CF_2. + Cl.$ $CF_3Cl \leftrightarrow CF_3. + Cl.$ $CF_3CF_2. + CH_3. \leftrightarrow CF_3CF_2CH_3$ $CF_3CF_2CH_3 \leftrightarrow CF_3CF=CH_2 + HF$ $Cl. + Cl. \leftrightarrow Cl_2$ B. Contacting Step—Formula (I) is $CH_4$ and/or $CH_3Cl$ Applicants have discovered that compounds such as the preferred $CH_4$ and $CH_3Cl$ can be reacted with compounds of Formula (II) to synthesize compounds such as $CF_3CF=CH_2$ (HFO-1234yf). In certain preferred embodiments, the contacting step includes a reaction of the type in which a certain flow of the compound of Formula (II), such as 50 sccm of $CF_3CFHCl$, together with a flow of the compound of Formula (I), such as 30 sccm of methane or $CH_3Cl$, is introduced together with a flow of air (e.g., about 20 sccm) into a reaction vessel, which may include a pre-heater operating at a relatively elevated temperature, for example, from about 400° C. to about 800° C. (preferably in certain embodiments at about 450° C.) containing the appropriate amount and type of catalyst in accordance with the present invention (for gas flows of the quantity mentioned in this paragraph, a bed of 100 cc of nickel catalyst kept in a 1-inch Monel reactor at about 350° C. to about 675° C.). In certain embodiments, the effluent gas mixtures from the reactor may be passed through a 20% aqueous KOH solution to neutralize any HF formed during the reaction to KF and $H_2O$.

Certain preferred methods for catalyst preparation are described below, and the catalysts prepared in accordance with this description were used in and are referred to in the experiments described in the examples which follow.

Catalyst Preparation

Catalyst A1

About 100 cc Ni-mesh is used as the catalyst.

Catalyst B1

About 100 cc Ni-mesh is charged in the reactor and then reduced with 20 SCCM of $H_2$ at 650° C. for 6 hours. This pre-reduced catalyst is used in the reaction.

Catalyst C1

About 1.5 gm to 2.0 gm of Ni (II) hexafluoroacetylacetonate hydrate is dissolved in 200 cc of methanol at about 55° C. and then about 100 cc of dried activated carbon (⅛-inch cylinders) was gradually mixed with the precursor solution. The methanol was evaporated slowly under vacuum at room temperature and then dried in an oven under vacuum at 100° C. for 10 hour.

The dried mass was then charged into the 1-inch Monel reactor and then reduced with 20 sccm of $H_2$ at 550° C. for 6 hours and then about 2 hours at 650° C. The catalyst was finally then calcined under 20 sccm of $N_2$ at 700° C. for about ½ hour.

Catalyst D1

5 gm of $La_2NiO_4$ was prepared by adopting the citric acid complexing method. Stoichiometric amounts of nickel and lanthanum nitrates were dissolved in an aqueous solution. After a little excess of citric acid was added, the solution was evaporated by vigorously stirring at 70° C. to generate viscous syrup. To this syrup was added 50 ml of methanol and 100 cc of dried activated carbon. The resultant material was then dried in an oven at about 180° C. for about 1 hour followed by calcinations at about 500° C. for about 2 hours and then at 900° C. for 6 hours. The catalyst was finally reduced with 25 sccm of $H_2$ at 750° C. for 8 hours.

Catalyst E1

Pd/C was prepared using 3 gm of Pd (II) acetylacetonate as the precursor and following the procedure used to prepare catalyst E.

Catalyst F1

Powder BaO was obtained from Aldrich and used after drying at about 450° C. under about 20 sccm of $N_2$ for about 12 hours.

Catalyst G1

Powder BaO was dispersed in an anhydrous solvent and then added a colloidal solution of 1 gram of Ni in methanol to the mixture. The solvent was evaporated slowly under vacuum at room temperature and then dried in an oven under vacuum at 100° C. for 1 about 10 hours.

The dried mass was then charged into the 1-inch monel reactor and then dried at 550° C. for 6 hours and then calcined under about 20 sccm of $N_2$ at 700° C. for about ½ hours.

Examples

Section B

Table B 1 shows results of the experiments using different starting CFCs under substantially identical conditions. The reaction between methane and $CF_3CFHCl$ gave 22% $CF3CF=CH_2$ (HFO-1234yf). A similar conversion to HFO-1234yf was achieved when methyl chloride was used as the reactant in the place of methane. A conversion of about 12% was achieved in the limiting reactant when $CF_2HCl$ was used as one of the reactants. In the presence of air, $CO_2$ was a major byproduct; carbon black was a main by-product in the absence of air.

TABLE B1

Effect of different starting reaction on the HFO-1234yf production rate[a]

| Reaction | T, ° C. | P, psig | Conv. of CFC mol % | Conv. of CFC to 1234yf mol % | Byproducts mol % |
|---|---|---|---|---|---|
| $CF_3CFHCl$ + $CH_4$ + Air | 650 | 1.6 | 75 | 22 | $CF_3CFH_2$(16%); $C_2F_3H$ (6%); $CF_3Cl$ (4%); $CHF_3$(10%); $CCl_4$(3%); $CHCl_3$ (1%); $CO_2$(28%), and C(6%); Unknown (5%) |
| $CF_3CFHCl$ + $CH_3Cl$ + Air | 675 | 3.2 | 82 | 23 | $CO_2$(22%); $CF_3CFH_2$ (10%); $CF_3Cl$(9%), $CF_2Cl_2$(6%), $CF_3CF_2Cl$(5%), $CF_3CF_2H$(2%); $C_2F_6$(2%), C(8%); $CCl_4$(2%); Unknown (5%) |
| $CF_3CFHCl$ + $CH_3Cl$ | 715 | 5 | 100 | 1 | C(62%); $CF_3H$(2%); $CF_3Cl$(18%); $CF_3CFH_2$(8%); Unknown (9%) |
| $CF_3CFCl_2$ + $CH_4$ + Air | 650 | 6 | 83 | 12 | $CF_3CFHCl$(21%); $CF_3CFH_2$(4%); $CO_2$(36%), C(6%); $CF_3H$(4%); $CF_3Cl$(12%); Unknown (5%) |
| $CF_2HCl$ + $CH_3Cl$ + Air | 690 | 3 | 100 | 2 | C(26%), CO2(40%), $C_2F_4$(2%), $C_2F_3Cl$(2%), CHF3(5%), CF3Cl(6%), $CF_4$(3%); unknown 14% |
| $CF_3CF_2H$ + $CH_4$ + Air | 600 | 3 | 16 | 1 | $CO_2$(60%), C(10%); $CF_3CF_2CF_2CF_3$(2%), $CHF_3$ (14%), $C_2F_4$(4%), $C_2F_6$(9%) |
| $CHF_3$ + $CH_3Cl$ | 650° C. | 5 | 42 | 1 | C (60%), $CH_3F$(24%), $CH_2F_2$(4%), $C_2F_4$(2%); $CCl_4$(2%), Unknown (7%) |

[a]Reaction conditions: CFCs, 50 SCCM; $CH_4$ or $CH_3Cl$, 30 SCCM; Air, 20 SCCM; Catalyst, Ni-mesh; Amount of catalyst, 100 cc; Conversion is the ratio of moles of CFC converted and moles of CFC taken initially × 100; 1234yf % = Moles of CFC converted to 1234yf/total moles of CFC taken initially × 100

Table B2 below shows the effect of different process parameters such as reaction temperature, pressure, flow rates, and composition of catalysts. The highest conversion (26%) to the preferred product (HFO-1234yf) was obtained using the conditions given in Table B2, Run 17 or 20 using Catalyst D1 or Catalyst G1.

TABLE B2

Parameter studies for the reaction of $CF_3CFHCl$ and $CH_4$ in the presence of Air

| Run | T, ° C. | P, psig | $CF_3CFHCl$, SCCM | $CH_4$, SCCM | Air, SCCM | Cat | Conv. of $CF_3CFHCl$, mol % | Conv. to 1234yf, mol % |
|---|---|---|---|---|---|---|---|---|
| 1 | 550 | 1.6 | 50 | 30 | 20 | A1 | 46 | 4 |
| 1 | 650 | 1.6 | 50 | 30 | 20 | A1 | 75 | 22 |
| 2 | 700 | 2 | 50 | 30 | 20 | A1 | 93 | 21 |
| 3 | 750 | 1.8 | 50 | 30 | 20 | A1 | 100 | 12 |
| 4 | 650 | 10 | 50 | 30 | 20 | A1 | 75 | 22 |
| 5 | 650 | 15 | 50 | 30 | 20 | A1 | 78 | 20 |
| 6 | 650 | 2 | 30 | 30 | 20 | A1 | 79 | 21 |
| 7 | 650 | 2 | 70 | 30 | 20 | A1 | 62 | 19 |
| 8 | 650 | 2 | 100 | 30 | 20 | A1 | 36 | 9 |
| 9 | 650 | 2 | 50 | 20 | 20 | A1 | 69 | 18 |
| 10 | 650 | 2 | 50 | 40 | 20 | A1 | 78 | 23 |
| 11 | 650 | 2 | 50 | 60 | 20 | A1 | 82 | 19 |
| 12 | 650 | 2 | 50 | 30 | 10 | A1 | 75 | 17 |
| 13 | 650 | 2 | 50 | 30 | 40 | A1 | 83 | 15 |
| 14 | 650 | 2 | 50 | 30 | 60 | A1 | 84 | 9 |
| 15 | 650 | 2 | 50 | 30 | 20 | B1 | 100 | 25 |
| 16 | 650 | 2 | 50 | 30 | 20 | C1 | 98 | 18 |
| 17 | 650 | 2 | 50 | 30 | 20 | D1 | 82 | 26 |

TABLE B2-continued

Parameter studies for the reaction of $CF_3CFHCl$ and $CH_4$ in the presence of Air

| Run | T, °C. | P, psig | $CF_3CFHCl$, SCCM | $CH_4$, SCCM | Air, SCCM | Cat | Conv. of $CF_3CFHCl$, mol % | Conv. to 1234yf, mol % |
|---|---|---|---|---|---|---|---|---|
| 18 | 650 | 2 | 50 | 30 | 20 | E1 | 69 | 6 |
| 19 | 650 | 2 | 50 | 30 | 20 | F1 | 67 | 16 |
| 20 | 650 | 2 | 50 | 30 | 20 | G1 | 75 | 26 |

A1 is Ni-mesh; B1 is Ni-mesh reduced; C1 is Ni/C; D1 is $La_2NiO_4$; E1 is Pd/C; F1 is BaO; G1 is Ni/BaO $CF_3CFHCl \rightarrow CF_3CFH. + Cl.$
$CH_4 + Cl. \rightarrow CH_3. + HCl$
$CF_3CFH. + CH_3. \rightarrow CF_3CFHCH_3$
$CF_3CFHCH_3 + 1/2 O_2 \rightarrow CF_3CF=CH_2 + H_2O$

Having thus described a few particular embodiments of the invention, various alterations, modifications, and improvements will readily occur to those skilled in the art. Such alterations, modifications, and improvements, as are made obvious by this disclosure, are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A process for the preparation of fluorinated olefins having three carbon atoms comprising:
   contacting a compound of Formula (I)

$$C(R^1_a R^2_b R^3_c) \tag{I}$$

with a compound of Formula (II)

$$C(R^1_a R^2_b R^3_c)C(R^1_a R^2_b R^3_c) \tag{II}$$

wherein $R^1$, $R^2$, and $R^3$ are each independently H or a halogen selected from the group consisting of fluorine; chlorine, bromine and iodine, provided that the compound of Formula (I) has at least three halogen substituents and that said at least three halogen substituents comprise at least one fluorine; a, b and c are each independently 0, 1, 2 or 3; said contacting step being carried out in the presence of a metal-based catalyst wherein said metal is selected from the group consisting of Ni, Pd, Sb, Al, and Fe to produce at least one tetrafluoropropene.

2. The process of claim 1 wherein said contacting step is effective to convert at least about 50% of said compound of Formula (II).

3. The process of claim 1 wherein said contacting step is effective to convert at least about 70% of said compound of Formula (II).

4. The process of claim 1 wherein said contacting step is effective to convert at least about 90% of said compound of Formula (II).

5. The process of claim 1 wherein said contacting step comprises a reacting step where at least one Formula (I) compound is reacted with at least one Formula (II) compound in the presence of a catalyst wherein said reacting step is effective to produce a reaction product having at least about 20% selectivity to one or more tetrafluoropropenes.

6. The process of claim 5 wherein said reacting step is effective to produce a reaction product having at least about 40% selectivity to one or more tetrafluoropropenes.

7. The process of claim 5 wherein said reacting step is effective to produce a reaction product having at least about 70% selectivity to one or more tetrafluoropropenes.

8. The process of claim 1 wherein said contacting step comprises a reacting step where at least one Formula (I) compound is reacted with at least one Formula (II) compound in the presence of a catalyst; wherein said reacting step is effective to produce a reaction product comprising HFO-1234yf.

9. The process of claim 8 wherein said reacting step is effective to produce a reaction product having at least about 20% selectivity to one or more HFO-1234yf.

10. The process of claim 8 wherein said reacting step is effective to produce a reaction product having at least about 70% selectivity to one or more HFO-1234yf.

11. The process of claim 8 wherein said reacting step comprises a gas phase reaction.

12. The process of claim 1 wherein said contacting step comprises introducing into a reactor one or more compounds of Formula (I) and one or more compounds of Formula (II) in a Formula (II):Formula (I) mole ratio of from about 0.5:1 to about 10:1.

13. The process of claim 12 wherein said Formula (II) in a Formula (II):Formula (I) mole ratio is form about 1:1 to about 3:1.

14. The process of claim 1 wherein said Formula (I) compound comprises $CF_3Cl$.

15. The process of claim 1 wherein said Formula (II) compound comprises $CH_3CF_2Cl$.

16. The process of claim 15 wherein said $CH_3CF_2Cl$ and $CF_3Cl$ are present in a $CH_3CF_2Cl:CF_3Cl$ mole ratio of about 1:1 to about 4:1.

17. The process of claim 16 wherein said $CH_3CF_2Cl:CF_3Cl$ mole ratio is from about 1.5:1 to about 2.5:1.

18. The process of claim 1 wherein said contacting step consists essentially of a reaction taking place in substantially one reaction vessel.

19. The process of claim 1 wherein said contacting step further comprises contacting said compounds of Formula (I) and Formula (II) in the presence of an oxygen-containing composition.

20. The process of claim 19 wherein said oxygen-containing composition comprises air.

21. A process for the preparation of fluorinated olefins having three carbon atoms comprising:
    contacting a first compound selected from the group consisting of $CH_4$ and $CH_3Cl$,
    with a second compound of Formula (II):

$$C(R^1_a R^2_b R^3_c)C(R^1_a R^2_b R^3_c) \tag{II}$$

wherein $R^1$, $R^2$, and $R^3$ are each independently H or a halogen selected from the group consisting of fluorine; chlorine, bromine and iodine, provided that the compound of Formula (II) has at least three fluorine; a, b and c are each independently 0, 1, 2, or 3, said contacting step being carried out in the presence of a metal-based catalyst wherein said metal is selected from the group consisting of Ni, Pd, Sb, Al, and Fe to produce at least one tetrafluoropropene.

22. The process of claim 21 wherein Formula (II) is a compound selected from the group consisting of $CF_3CFHCl$, $CF_3CFCl_2$, and $CF_3CF_2H$.

23. The process of claim 22 wherein said tetrafluoropropene is HFO-1234yf.

24. The process of claim 20 wherein said metal-based catalyst is a nickel-based catalyst.

25. The process of claim 24 wherein said metal-based catalyst is selected from the group consisting of nickel mesh, Ni/C, $La_2NiO_4$, Ni/BaO, Ni/CaO, and Ni/MgO.

* * * * *